United States Patent

Berg

Patent Number: 6,164,144
Date of Patent: Dec. 26, 2000

[54] METHOD AND DEVICE FOR SOLID PHASE MICROEXTRACTION

[75] Inventor: John R. Berg, Davis, Calif.

[73] Assignee: Varian, Inc., Palo Alto, Calif.

[21] Appl. No.: 08/993,688

[22] Filed: Dec. 18, 1997

[51] Int. Cl.$^7$ .................................................. G01N 13/00
[52] U.S. Cl. ...................................... 73/863.21; 73/864.83
[58] Field of Search ........................... 73/863.01, 863.12, 73/863.21, 864.21, 864.22, 864.23, 864.24, 864.81, 864.87, 61.55, 61.56; 436/178; 422/89

[56] References Cited

U.S. PATENT DOCUMENTS

| | | | |
|---|---|---|---|
| 4,476,734 | 10/1984 | Banks et al. | 73/864.22 |
| 4,732,046 | 3/1988 | Lawrence et al. | 73/864.21 |
| 5,565,622 | 10/1996 | Murphy | 73/61 |
| 5,691,206 | 11/1997 | Pawliszyn | 73/863.21 |

FOREIGN PATENT DOCUMENTS

91/15745  10/1991  WIPO .

OTHER PUBLICATIONS

Article by Louch et al., entitled "Dynamics of Organic Compound Extraction from Water Using Liquid–Coated Fused Silica Fibers," published in *Anal. Chem.* in 1992, in vol. 64, pp. 1187–1199.

*Primary Examiner*—Robert Raevis
*Attorney, Agent, or Firm*—Edward H. Berkowitz

[57] ABSTRACT

An improved method and apparatus are described for carrying out SPME onto the inner surface of a syringe needle at least partially coated with a stationary phase followed by desorption of analytes from a sample into a gas chromatograph injector for analysis. The SPME apparatus comprises a syringe having a syringe barrel and a plunger slidable within one end of the barrel, a hollow needle extending from the other end of the barrel and having its inner surface coated with the stationary phase, and fluid communication means for transferring a fluid into contact with the coated inner surface of said hollow needle. During the analysis phase, a carrier gas is transferred into contact with the coated inner surface. A valve means can be used to switch the flow of sample from a container containing the sample during the microextraction phase to the carrier gas during the analysis phase. In a preferred embodiment of the present invention, the carrier gas is preheated before passing into the syringe during the analysis phase.

10 Claims, 6 Drawing Sheets

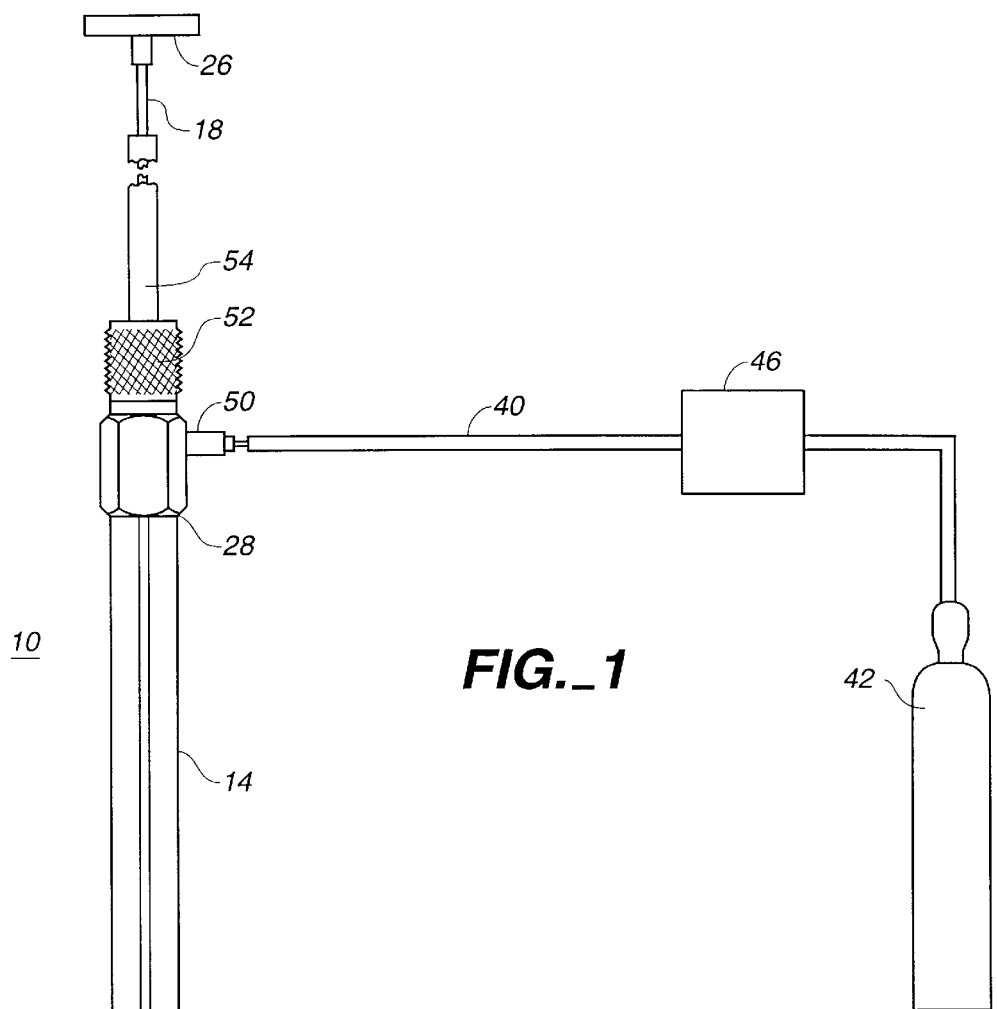
FIG._1
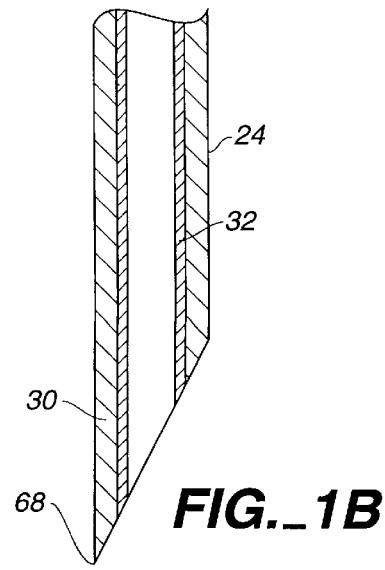
FIG._1B

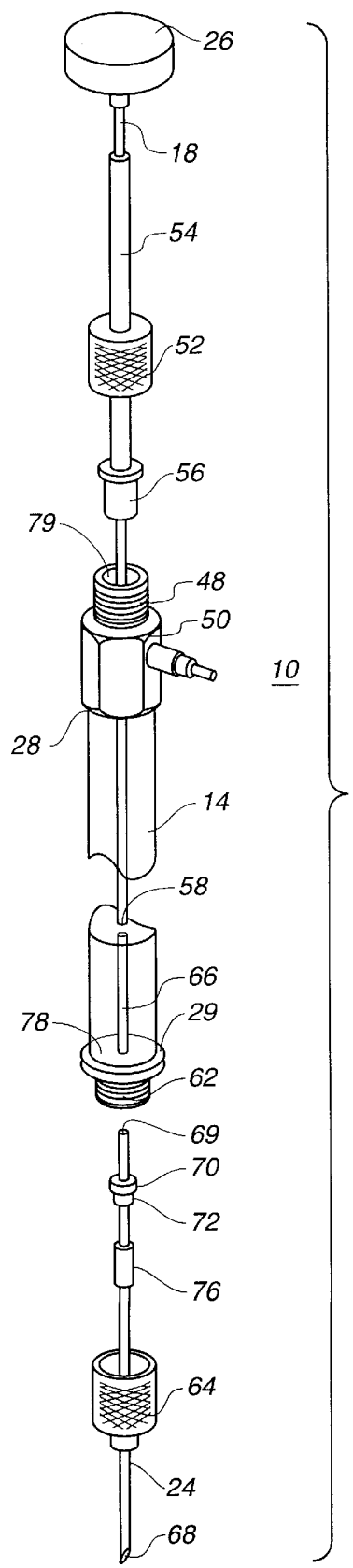
FIG._1A

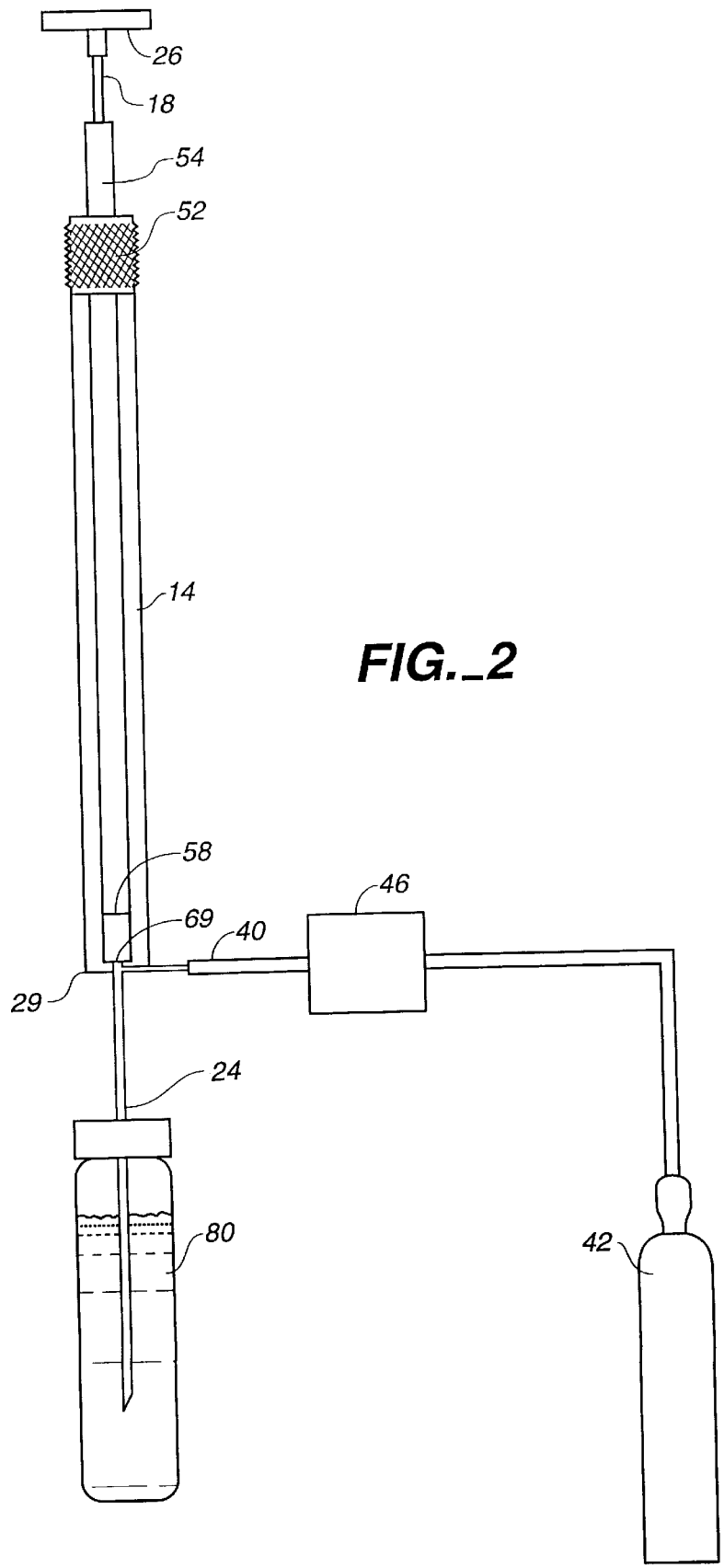
FIG._2

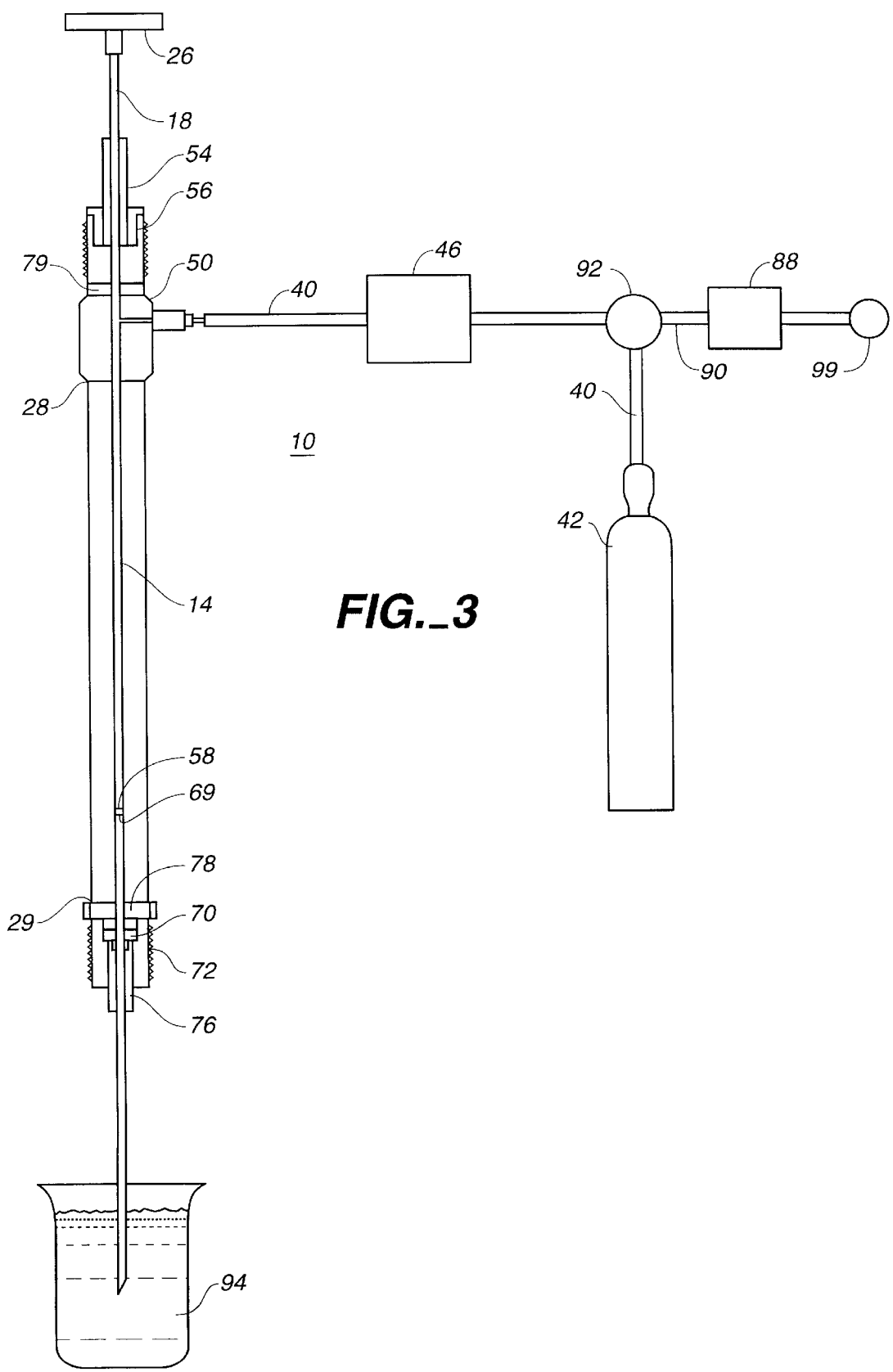
FIG._3

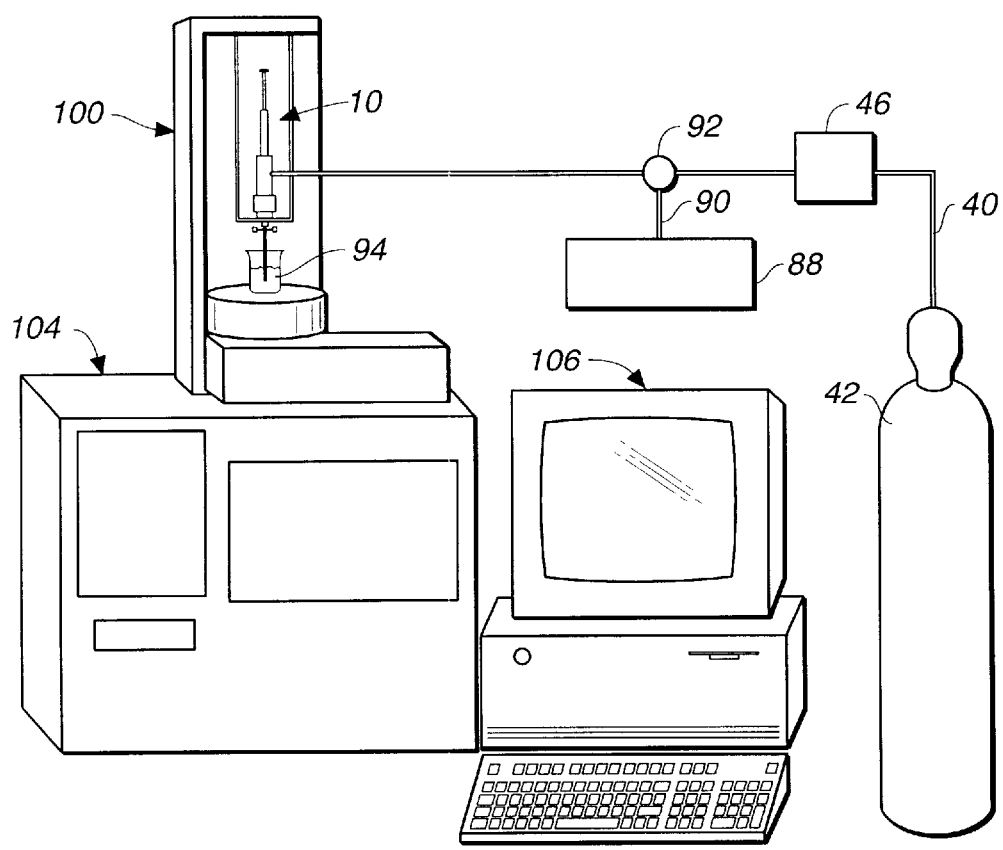
FIG._4

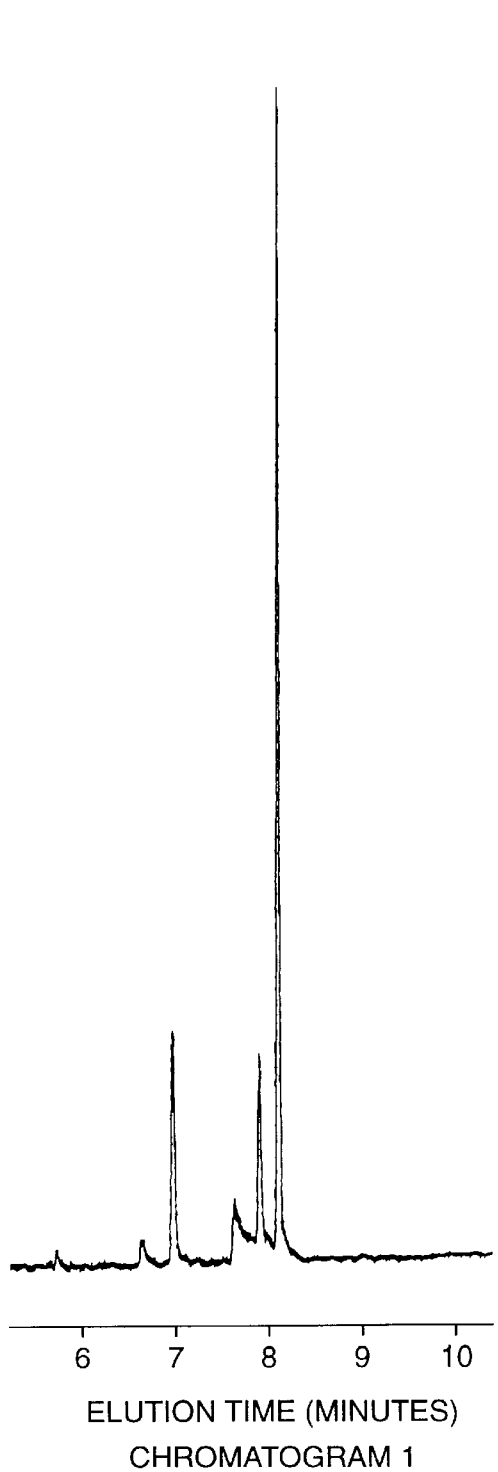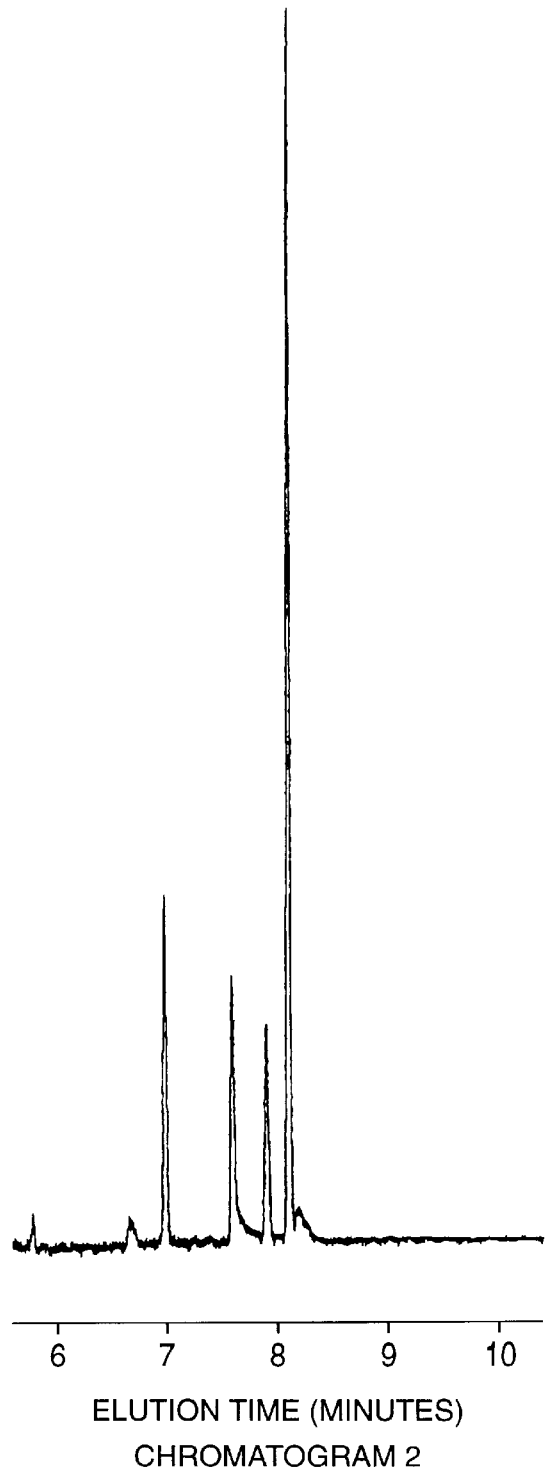
ELUTION TIME (MINUTES)
CHROMATOGRAM 1
*FIG._5A*
ELUTION TIME (MINUTES)
CHROMATOGRAM 2
*FIG._5B*

METHOD AND DEVICE FOR SOLID PHASE MICROEXTRACTION

FIELD OF THE INVENTION

This invention relates to improved an method and device for solid phase microextraction and analysis. In particular, this invention relates to an improved method and device over the prior art method and device for microextraction using a coated needle to absorb components of interest from a liquid sample and to desorb the components during analysis.

BACKGROUND OF THE INVENTION

The organic analyses of environmental samples involve the separation of analytes (components) of interest from such matrices as soil, water, fly ash, tissue or other material. Liquid extraction is traditionally used as the separation process. For example, water samples are usually extracted with organic solvent. Similarly, solid samples are leached with an organic solvent in a SOXHLET apparatus. Methods based on solvent extraction are often time consuming, difficult to automate and are very expensive since they require high purity organic solvents and these organic solvents involve significant purchase and disposal costs. Further, the organic samples may have high toxicity and often are difficult to work with. In addition, the extraction processes can be highly nonselective. Therefore, sequential chromatographic techniques must sometimes be used to separate complex mixtures after extraction, significantly increasing the overall analysis time and the cost.

Solid phase extraction is a known effective alternative to-liquid-liquid extraction in the analysis of aqueous samples. The primary advantage of solid phase extraction is the reduced consumption of high purity solvents and the resulting reduction in laboratory costs and solvent disposal costs. Solid phase extraction also reduces the time required to isolate the analytes of interest. However, solid phase extraction continues to use solvents and often suffers from high blank values. Further, there is considerable variation between the products offered by different manufacturers and lot-to-lot variation can be a problem when carrying-out solid phase extraction procedures. Solid phase extraction-cartridges available from manufacturers are typically constructed of plastic, which can adsorb the analytes and increase interferences in the analysis. The disposable plastic cartridges used in the solid phase extraction process are first activated using organic solvent. The excess organic solvent is then removed and the sample to be tested is passed through the cartridge. The organic analytes from the sample are adsorbed on the chemically modified silica surface of the material in the cartridge. Both molecules of interest as well as interferences are retained on the cartridge material. During desorption, a selective solvent is chosen to first remove the interferences. The analyte is then washed out of the cartridge. The analytical procedure from that point on is identical to that used in liquid-liquid extraction. The analyte is first pre-concentrated by evaporating down the extract and the mixture is then injected into an appropriate high resolution chromatographic instrument. Steps involving the use of organic solvents are the most time consuming.

Solid phase microextraction, or SPME, was developed as the alternative to the foregoing prior art methods of preparing samples in a fluid carrier for chromatographic analysis; see Pawliszyn, Janusz, WO 91/15745, International Publication Date of Oct. 17, 1991. SPME involves using a fiber that is mounted within a hollow needle of a syringe, e.g. a modified gas chromatography (GC) syringe. The fiber, for example a fused silica fiber coated with an adsorbent or a stationary phase, acts as a "sponge" to extract a sample and to concentrate the organic analytes on its surface so that it can be transferred into the heated injector of the GC. While in the injector, the analytes are thermally desorbed from the fiber and transferred into the GC column for analysis. With SPME, one can achieve detection limits down to the parts-per-trillion (ppt) range for a wide number of volatile and semi-volatile compounds. Pertinent portions of the Pawliszyn reference that define details of the SPME unit are incorporated by reference herein.

The chief disadvantage of the use of SPME is the time required to extract the sample by the coated fibers. For example, when a water matrix sample containing one or more analytes of interest is desired to be analyzed and is contained in a typical sample vial containing a septum, the needle of the syringe of the SPME device is inserted through the septum. The plunger of the syringe is depressed and the exposed coated fiber extends from the free end of the needle and is inserted either above (headspace sample) or into the water matrix sample (liquid sample). In this manner, the fiber will not be damaged by the septum of the sample vial. For example, organic analytes that may be found in water can be extracted into a non-polar phase coated onto the fiber. Water is considered to be the carrier in a water matrix sample. When the microextraction has occurred to a sufficient degree, the plunger is moved to the withdrawn position causing the fiber to be drawn into the needle and the needle is removed from the sample bottle through the septum. The time for fiber adsorption of the analytes to be extracted will depend on many factors including the analytes themselves as well as the thickness and type of coating, if any, on the fiber. Typically the equilibrium adsorption time ranges from 1 to 30 minutes, with some analytes requiring up to several hours. In the preferred method of operating SPME, the sample is stirred or the vial is rotated to impart forceful agitation of the sample during the time the fiber is present in the vial during the extraction stage of the analysis in order to decrease the adsorption time. The stirring can be done by placing a magnetic bar within the analyte and by using a conventional magnetic stirrer. Another method for agitation is to induce ultrasonic vibrations within the liquid sample in the vial. It has been found that the adsorption time can be reduced from about 30 minutes range to approximately two minutes with forceful agitation; see FIG. 9 at page 1194 of D. Louch, S. Motlagh, and J. Pawliszyn, *"Dynamics of Organic Compound Extraction From Water Using Liquid-Coated Fused Silica Fibers"*, Analytical Chemistry, Vol. 84, No. 10, pages 1187–1199 (May 15, 1992).

After the extraction stage, the plunger is moved to a withdrawn position to retract the fiber within the needle and the needle is removed from the bottle. During the analysis stage, the needle is inserted through the septum of an injection port of a conventional gas chromatograph or other suitable analytical instrument and the analytes are then desorbed into the injector port.

It has been found that to provide sufficient sample agitation to significantly reduce the adsorption time using the above method, mechanical and electrical part damage can occur. Under some cases of forceful agitation, the vials have been known to crack and even to break. In addition, the use of magnetic, ultrasound and other conventional stirring means added to the sample introduces a potential source of contamination. A disadvantage of using ultrasound agitation of the sample is the unwanted rise in the temperature of the sample which adds an unwanted and uncontrollable variable to the analysis since adsorption efficiency is temperature dependant. Another disadvantage of the prior art SPME technique is the slow rate of absorption as a result of the coating thickness of the stationary phase on the fibers. The coating thickness is dictated by the capacity of the stationary phase to absorb the analytes.

Murphy, U.S. Pat. No. 5,565,622, discloses a method for overcoming many of the problems of the previous SPME method by microextraction onto the inner surface of a syringe needle at least partially coated with the stationary phase followed by desorption of the absorbed components into the gas chromatograph injector, either thermally or using a solvent flush. If the components are thermally desorbed from the inner surface of the needle, there is an inefficient transfer into the chromatographic column. The first problem with thermal desorption is that as the needle heats up, the absorbed components vaporize, but are not swept into the injector by any directing force. Secondly, since the needle is inserted into the pressurized zone of the injector, the pressurized carrier gas tends to reverse flow through the needle causing loss of sample. This is the case because the syringe plunger/barrel assembly commonly have leaks. On the other hand if a solvent flush is used, one of the chief advantages of using the SPME method is negated. This is true because the peak of the chromatogram for the solvent interferes with the peaks for the components under analysis. Finally, Murphy also discloses using cryotrapping of the components of interest on the head of the chromatographic column prior to analysis. Cryotrapping is a known method for increasing column efficiency, i.e., obtaining good component peak shapes. The problem with using cryotrapping is that the amount of analytes present in a given sample vial are the maximum that can be absorbed onto the stationary phase by the Murphy method.

There is a need for an alternative method to improve the rate of desorption without the necessity of using either thermal desorption or a solvent flush of the prior art methods. There is also a need to increase the amount of analytes that can be absorbed onto the coated needle than with the cryotrapping methods of the prior art.

SUMMARY OF THE INVENTION

The present invention is an improvement in the prior art method and device for carrying out SPME onto the inner surface of a syringe needle at least partially coated with a stationary phase followed by desorption of analytes adsorbed onto the stationary phase into a gas chromatograph injector. The device of the present invention comprises a syringe having a syringe barrel and a plunger slidable within one end of the barrel, a hollow needle extending from the other end of the barrel and having its inner surface coated with the stationary phase, and fluid communication means for transferring a fluid into contact with the coated inner surface of said hollow needle. The method of the present invention comprises initially contacting the coated inner surface of the hollow needle with a sample containing the analytes for a sufficient time to allow their microextraction and then placing the needle into an injection port of an chromatographic instrument and flowing a carrier gas through the fluid communication means to assist in the desorption of the analytes from the coated surface into the injection port.

In a preferred embodiment of the present invention the fluid communication means passes through a heat exchange or other means for heating the carrier gas to increase the rate of desorption of the analytes.

BRIEF DESCRIPTION OF THE DRAWINGS

FIG. 1 is a schematic view of one embodiment of the SPME device of the present invention and illustrates a side arm communication means for a carrier gas to desorb analytes contained in a sample from the inner surface of the syringe needle into an injection port of a gas chromatograph during analysis;

FIG. 1A is an exploded front view of one type of syringe of the SPME device shown in FIG. 1 in which a fluid communication side arm is connected to the barrel of the syringe;

FIG. 1B is exploded partial front view of the lower end of the coated needle of the SPME device shown in FIG. 1;

FIG. 2 is a schematic view of another embodiment of the SPME device of the present invention and illustrates another type of syringe in which the side arm fluid communication means for the carrier gas is connected to the syringe needle;

FIG. 3 is a schematic view of still another embodiment of the SPME device of the present invention and illustrates a valve means for switching from the flow of sample onto the inner surface of the syringe needle during the microextraction of analytes to the flow of carrier gas during analysis;

FIG. 4 is a perspective view of one embodiment of the SPME of the present invention in combination with an SPME autosampler unit, a GC unit or other suitable analytical instrument and a personal computer programmed to operate the combination;

FIG. 5A shows Chromatogram 1 obtained using an SPME device of the prior art; and FIG. 5B shows Chromatogram 2 obtained using the embodiment of the SPME device of the present invention shown in FIG. 1.

DETAILED DESCRIPTION OF THE INVENTION

Referring to FIG. 1, syringe 10 is shown in the desorption or analysis mode mounted above injection port 12 of a conventional gas chromatograph. Syringe 10 comprises syringe barrel 14, plunger 18 slidably mounted within barrel 14, and hollow needle 24. Plunger 18 has handle 26 extending from upper end 28 of barrel 14 for manual operation of syringe 10. Hollow needle 24 is located at the lower end 29 of barrel 18 and has inner surface 30 coated with stationary phase 32. Stationary phase 32 can cover the entire inner surface of needle 24 or a portion thereof depending on the type of coating and the particular analytes of interest.

The fluid communication means comprises flow line 40 for the passage of a carrier gas stored in gas cylinder 42 to syringe 10. The carrier gas is inert to the analytes of interest, e.g, xenon, helium and nitrogen, Preferably, the carrier gas is passed through heat exchange 46 or other suitable means for heating the carrier gas to temperatures in the range of about 50° to 200° C. to improve the desorption of the analytes during the analysis mode.

FIG. 1A shows an exploded view of one specific embodiment of syringe 10 which is commercially available as VARIAN 8200 Autosampler syringe. Flow line 40 is joined to side arm tee 50, preferably consisting of stainless steel, sealingly attached to upper end 28 of syringe barrel 14 preferably consisting of transparent engineering plastic or glass. Upper syringe cap 52, also preferably consisting of stainless steel is threaded onto threaded projection 48 of side arm tee 50 to serve as an upper fastener. Plunger 18 extends from handle 26 through a central opening in one end of plunger guide 54, upper syringe cap 52 and plunger guide and thrust assembly integrally formed in the other end of plunger guide 54 to plunger tip 58, preferably consisting of an engineering plastic, e.g. polytetrafluoroethylene (PTFE), adjacent lower end 29 of barrel 14. Lower threaded member 62, preferably consisting of stainless steel, is sealingly attached to lower end 29. Lower syringe cap 64, also preferably consisting of stainless steel, is threaded onto the threaded member 62 to serve as a lower fastener. The length of syringe 10 from upper syringe cap 52 to lower syringe cap 64 is about 18 cm., the outside diameter of syringe barrel 14 is about 0.8 cm., and the inside diameter of barrel 14 is about 0.14 cm. Compartment 66 of barrel 14 contains graduated markings (not shown) along its length at 0.2 microliter increments from 0 to 10 microliters. Hollow needle 24 extends from tip 68 at its free end through a central opening in lower syringe cap 64 to end 69 adjacent plunger tip 58, when plunger 18 is in the fully depressed position. Needle 24 passes through and is fixedly attached to needle seal 70, preferably consisting of PTFE, and needle stop 72, preferably consisting of stainless steel. Spring 76 encircles the portion of needle 24 extending through lower cap 64 and needle stop 72. Grommet 78 is provided within threaded member 62 at lower end 29, preferably consisting of Teflon, to prevent any leakage of sample. Similarly, grommet 79 is provided within threaded projection 48 at upper end 28.

The SPME method and analysis consists of a few simple steps. For example, when a sample in sample vial 80 containing analytes of interest is desired to be analyzed as shown in FIG. 2, handle 26 is used to depress plunger 18 so that plunger tip 58 is immediately adjacent end 69 of needle 24 with tip 68 of the needle 24 extending into vial 80. Plunger 18 is retracted and the sample is aspirated into barrel 14 and then plunger is depressed and the sample redispensed into vial 80. This is repeated a number of times until the desired amount of analytes are adsorbed onto stationary phase 32. The exact time for extraction will depend on many factors including the analytes being extracted as well as the thickness and type of stationary phase. Usually, the extraction time is approximately two minutes. Needle 24 is then inserted through septum 84 in an injection port 12 of a conventional GC or other suitable analytical instrument as shown in FIG. 1. A carrier gas is fed through insulated flow line 40 from gas cylinder 42 through the length of barrel 14 and needle 14. A portion of the carrier gas passes into the pores of stationary phase 32 to flush the analytes into the bulk of the carrier gas and into GC for analysis. Preferably, the carrier gas is heated in heater 46 to greatly decrease the desorption time.

FIG. 2 shows the alternate embodiment in which carrier gas side arm 90 is mounted onto lower end 29 of barrel 14 and the carrier gas in flow line 40 is in direct fluid communication with hollow needle 24. The carrier gas from cylinder 42 and passing through heater 46 avoids having to pass through barrel 14, but passes directly into contact with stationary phase 32 without attendant heat loss.

Another embodiment of the present invention is shown in FIG. 3 to provide an improved microextraction step. In this embodiment, a stream of the sample in container 88 is pressurized into syringe 10 through flow line 90, three-way valve 92, flow line 40 and side arm tee 50 and out syringe 10 into beaker 94 by pressurizing means 99. The microextraction step is continued until sufficient analytes have been adsorbed into stationary phase 32. During the analysis step, valve 92 diverts the carrier gas through flow line 40 and syringe 10 as described above.

The device and method of the present invention preferably utilizes a mechanical device such as SPME autosampler 100 in combination with analytical instrument 104 depicted in FIG. 4. Autosampler 104 can be programmed and operated by personal computer 106 to operate valve 92 during the extraction state and to insert needle 14 into the injection port of the GC 104. The only difference between this embodiment of the present invention and that shown in FIG. 3 is that only the carrier gas is passed through heater 46 in the embodiment shown in FIG. 4.

COMPARATIVE EXAMPLE

Chromatograms 1 and 2 respectively shown in FIGS. 5A and 5B were obtained using the SPME device of the present invention and the device described and claimed in Murphy, U.S. Pat. No. 5,565,622. Specifically, Chromatograms 1 and 2 were obtained using a syringe designed very much like syringe 10 shown in FIGS. 1, 1A and 1B, except that needle 14 was replaced with a hollow DB-1™ column comprising fused silica manufactured by J & W Scientific having its inner walls coated with a film of polydimethylsiloxane to serve as the stationary phase. The hollow column, also referred to herein as the "needle", was 8 cm. long by 0.32 mm internal diameter and having a film thickness of 5 microns The tip of the "needle" was placed into a standard capillary column test mixture. Approximately one microliter of this mixture was drawn into the "needle" and held there for approximately 30 seconds. The sample was then expelled and the extraction phase was complete to leave analytes and some solvent absorbed into the liquid phase on the coated interior of the "needle". The "needle" was then placed into hot injection port 12 operating at 250° C. of GC column 104 to thermally desorb the analytes in the manner described in Murphy, U.S. Pat. No. 5,565,622. The detector used flame ionization at 300° C. The GC column was a DB-1 column having the dimensions of 30 meters by 0.25 mm and 0.25 $\mu$m film thickness. The GC column was programmed from an initial temperature of 80° C. (2 min. hold) to 240° C. at 20° per minute using a splitless injection port. Chromatogram 1 of FIG. 5A shows the resulting static desorption of this prior art method.

The same extraction method was carried out using the same "needle" and the "needle" was placed into injection port 12 of GC column 104. In place of the static thermal desorption method of the prior art, the analytes were desorbed in accordance with the dynamic desorption method and device of the present invention. Specifically, the analytes were desorbed using helium as the carrier gas flowing through flow line 40 and side arm tee 50 and then through the "needle" into injector 12. Chromatogram 2 of FIG. 5B shows the resulting dynamic desorption using the method and device of the present invention. A very clear difference is evident on comparing Chromatograms 1 and 2. The peak of interest in each of these chromatograms is dimethylaniline, which is a very polar basic compound. The diffuse peak for dimethylaniline at an elution time of about 7.7 minutes shown in FIG. 5A indicates the analyte was poorly desorbed using the method of the prior art. The sharp peak for dimethylaniline at about 7.7 minutes shown in FIG. 5B indicates the analyte was efficiently desorbed using the present method with the carrier gas flowing through the "needle." It was completely unexpected with the dynamic method of the present invention that the individual components would show such a dramatic effect. Another advantage of the method and device of the present invention is that no cryogenic trapping was necessary to achieve the desired sharp peak shapes since the initial GC column was operating at 80° C. and substantially above room temperature.

Without departing from the spirit and scope of this invention, one of ordinary skill in the art can make various changes and modifications to the method and device of the present invention to adapt them to various usages and conditions. As such, these changes and modifications are properly, equitably, and intended to be, within the full range of equivalents of the following claims.

What is claimed is:

1. A device for carrying out solid phase microextraction (SPME) and analysis of a liquid sample of analytes contained in a fluid carrier which comprises:
   a syringe having a syringe barrel with a first end and a second end and a plunger slidable within said barrel, said plunger having a handle extending from the first end of said barrel,
   a hollow needle extending from the second end of said barrel and having an inner surface coated with a stationary phase,
   a fastener mounted on said first end of said barrel having an opening for receiving said plunger therethrough,
   a fastener mounted on said second end of said barrel having an opening for receiving said hollow needle,
   a side arm tee integrally formed in said first end of said barrel
   a tube connected to said side arm tee for transferring fluid into contact with the coated inner surface of said hollow needle,
   wherein the sample contacts the coated inner surface until the analytes of interest are sufficiently diffused into the stationary phase during SPME and wherein said hollow needle is inserted into an injection port of a chromatographic instrument and a carrier gas flows through said tube and said side arm tee and into contact with said coated inner surface of said hollow needle to assist in desorption of the analytes from said coated inner surface during analysis.

2. The device of claim 1, further comprising a three-way valve means having a first way connected to said tube and a second way connected to a supply of carrier gas, a second tube connected between a third way and a sample supply of the liquid sample, said valve means for controlling the sequential steps of transferring the liquid sample from the sample supply through said second tube and said first tube to said syringe and contacting said coated inner surface during SPME and flowing the carrier gas from said supply through said first tube and contacting said coated inner surface during analysis.

3. The device of claim 2, further comprising an autosampler for holding said syringe wherein said autosampler is programmable to activate said three-way valve means to control the flow of the sample during SPME and the carrier gas during analysis.

4. The device of claim 1, wherein said tube passes through a heating means to heat the carrier gas to increase the rate of desorption of the analytes.

5. A method of carrying out solid phase microextraction (SPME) and analysis of a sample of analytes contained in a carrier using a syringe, said syringe having a syringe barrel, a hollow needle having an inner surface coated with a stationary phase, and fluid communication means for transferring fluid into contact with the coated inner surface of said hollow needle, for the sufficient time to allow microextraction of analytes, said method comprising contacting said coated inner surface with the sample for a sufficient time to allow microextraction of analytes, placing the needle into an injection port of an chromatographic instrument, and flowing a carrier gas from a carrier gas source through said fluid communication means to assist in desorption of the analytes from said coated surface wherein the microextraction and analysis are carried out automatically through the use of an autosampler and wherein said autosampler manipulates valve means to control the time the sample is transferred into contact with said coated inner surface during SPME and to activate the flow of carrier gas during the analysis.

6. A method of carrying out solid phase microextraction (SPME) and analysis of a sample of analytes contained in a carrier using a syringe, said syringe having a syringe barrel, a hollow needle having an inner surface coated with a stationary phase, tube for transferring fluid into contact with the coated inner surface of said hollow needle, and valve means in said tube for switching from the flow of the sample during SPME to the flow of the carrier gas during analysis; said method comprising flowing the sample though said tube and contacting said coated inner surface with the sample for a sufficient time to allow microextraction of analytes, placing the needle into an injection port of an chromatographic instrument, and flowing a carrier gas through said tube to assist in desorption of the analytes from said coated surface.

7. The method as claimed in claim 6, wherein the microextraction and analysis are carried out automatically through the use of an autosampler.

8. A device for carrying out solid phase microextraction (SPME) and analysis of a sample of analytes contained in a fluid carrier which comprises:
   a syringe having a syringe barrel with a first end and a second end and a plunger slidable within said barrel, said plunger having a handle extending from the first end of said barrel,
   a hollow needle extending from the second end of said barrel and having an inner surface coated with a stationary phase,
   fluid communication means for transferring fluid into contact with the coated inner surface of said hollow needle, said fluid communication means comprising a first tube connected to said syringe barrel, a second tube for transferring the sample to said first tube, and valve means operably connected to said first and second tubes for controlling the sequential steps of transferring the sample to said a syringe and contacting said coated inner surface during SPME and flowing the carrier gas through said first tube and contacting said coated inner surface during analysis,
   wherein the sample contacts the coated inner surface until the analytes of interest are sufficiently diffused into the stationary phase during SPME and wherein said hollow needle is inserted into an injection port of a chromatographic instrument and a carrier gas flows through said fluid communication means and into contact with said coated inner surface of said hollow needle to assist in desorption of the analytes from said coated inner surface during analysis.

9. A device for carrying out solid phase microextraction (SPME) and analysis of a sample of analytes contained in a fluid carrier which comprises:
   a syringe having a syringe barrel with a first end and a second end and a plunger slidable within said barrel, said plunger having a handle extending from the first end of said barrel,
   a hollow needle extending from the second end of said barrel and having an inner surface coated with a stationary phase,
   fluid communication means for transferring fluid into contact with the coated inner surface of said hollow needle, said fluid communication means comprising a first tube connected to said coated needle, a second tube for transferring the sample to said first tube, valve means operably connected to said first and second tubes for controlling the sequential steps of transferring the sample through said second tube and said first tube to said syringe and contacting said coated inner surface during SPME and flowing the carrier gas through said first tube and contacting said coated inner surface during analysis, said fluid communication means being connected to said coated needle adjacent the second end of said syringe barrel, wherein the sample contacts the coated inner surface until the analytes of interest are sufficiently diffused into the stationary phase during SPME and wherein said hollow needle is inserted into an injection port of a chromatographic instrument and a carrier gas flows through said fluid communication means and into contact with said coated inner surface of said hollow needle to assist in desorption of the analytes from said coated inner surface during analysis.

10. A device for carrying out solid phase microextraction (SPME) and analysis of a sample of analytes contained in a fluid carrier which comprises:

a syringe having a syringe barrel with a first end and a second end and a plunger slidable within said barrel, said plunger having a handle extending from the first end of said barrel, a hollow needle extending from the second end of said barrel and having an inner surface coated with a stationary phase, fluid communication means for transferring fluid into contact with the coated inner surface of said hollow needle, said fluid communication means comprising an autosampler for holding said syringe wherein said fluid communication means comprises a first tube connected to said syringe barrel, a second tube for transferring the sample to said first tube, and valve means operably connected to said first and second tubes for controlling the sequential steps of transferring sample through said second tube and said first tube to said syringe and contacting said coated inner surface during SPME and flowing carrier gas to said first tube and contacting said coated inner surface during analysis and said autosampler is programmable to activate said valve means to control the flow of the sample during SPME and the carrier gas during analysis, wherein the sample contacts the coated inner surface until the analytes of interest are sufficiently diffused into the stationary phase during SPME and wherein said hollow needle is inserted into an injection port of a chromatographic instrument and a carrier gas flows through said fluid communication means and into contact with said coated inner surface of said hollow needle to assist in desorption of the analytes from said coated inner surface during analysis.

* * * * *